US009816934B2

(12) United States Patent
Li et al.

(10) Patent No.: US 9,816,934 B2
(45) Date of Patent: Nov. 14, 2017

(54) LASER INDUCED BREAKDOWN SPECTROSCOPY (LIBS) APPARATUS WITH AUTOMATIC WAVELENGTH CALIBRATION

(71) Applicants: Qun Li, Newark, DE (US); Sean Xiaolu Wang, Wilmington, DE (US)

(72) Inventors: Qun Li, Newark, DE (US); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 0 days.

(21) Appl. No.: 15/412,357

(22) Filed: Jan. 23, 2017

(65) Prior Publication Data

US 2017/0219494 A1    Aug. 3, 2017

Related U.S. Application Data

(60) Provisional application No. 62/289,452, filed on Feb. 1, 2016.

(51) Int. Cl.
  *G01J 3/30* (2006.01)
  *G01N 21/71* (2006.01)
  *G01N 21/27* (2006.01)

(52) U.S. Cl.
  CPC ......... *G01N 21/718* (2013.01); *G01N 21/274* (2013.01)

(58) Field of Classification Search
  CPC ... G01N 21/274; G01N 21/718; G01J 3/0272; G01J 3/443; G01J 3/2823
  See application file for complete search history.

(56) References Cited

U.S. PATENT DOCUMENTS

| 6,275,740 | B1 * | 8/2001 | Smith, Jr. ................. G01J 3/28 700/108 |
| 6,418,383 | B1 * | 7/2002 | Wang ........................ G01J 3/28 702/194 |
| 7,394,537 | B1 | 7/2008 | Lindfors et al. |
| 7,999,928 | B2 | 8/2011 | Beckstead et al. |
| 2007/0188747 | A1 * | 8/2007 | Nelson ..................... G01J 3/02 356/300 |

(Continued)

OTHER PUBLICATIONS

Rui, Wang,"Methods of Data Processing for Trace Elements Analysis Using Laser Induced Breakdown Spectroscopy", Nov. 2015, Plasma Science and Technology, p. 944.*

*Primary Examiner* — Michael A Lyons
*Assistant Examiner* — Maurice Smith

(57) ABSTRACT

This invention discloses a laser induced breakdown spectroscopy (LIBS) apparatus with automatic wavelength calibration. The LIBS apparatus comprises a database of pre-obtained LIBS spectra of standard calibration samples. When the LIBS spectrum of a target sample is acquired, a processor unit calculates a cross correlation between the LIBS spectrum of the calibration sample and the spectrum of the target sample in reference to a possible wavelength shift between the two spectra. The exact wavelength shift between the two spectra is found where the cross correlation reaches a maximum value. The wavelength shift of the target spectrum is then corrected through an interpolation procedure and the wavelength shift corrected spectrum is analyzed to obtain the composition information of the target sample.

3 Claims, 3 Drawing Sheets

(56) References Cited

U.S. PATENT DOCUMENTS

| | | | | |
|---|---|---|---|---|
| 2007/0263213 A1* | 11/2007 | Stedman | ................... | G01J 3/02 |
| | | | | 356/328 |
| 2012/0033212 A1 | 2/2012 | Barefield, II | | |
| 2012/0044488 A1* | 2/2012 | Senac | ....................... | G01J 3/02 |
| | | | | 356/316 |
| 2016/0084709 A1* | 3/2016 | Day | ......................... | G01J 3/30 |
| | | | | 356/318 |

* cited by examiner

LASER INDUCED BREAKDOWN SPECTROSCOPY (LIBS) APPARATUS WITH AUTOMATIC WAVELENGTH CALIBRATION

REFERENCE TO RELATED APPLICATION

This application claims inventions which were disclosed in Provisional Patent Application No. 62/289,452, filed Feb. 1, 2016, entitled "LASER INDUCED BREAKDOWN SPECTROSCOPY (LIBS) APPARATUS WITH AUTOMATIC WAVELENGTH CALIBRATION". The benefit under 35 USC §119(e) of the above mentioned United States Provisional Application is hereby claimed, and the aforementioned application is hereby incorporated herein by reference.

FIELD OF THE INVENTION

This invention generally relates to a laser induced breakdown spectroscopy (LIBS) apparatus, and more specifically to a laser induced breakdown spectroscopy (LIBS) apparatus with automatic wavelength calibration.

BACKGROUND

Laser induced breakdown spectroscopy (LIBS) is a type of atomic emission spectroscopy which uses a highly energetic laser pulse as the excitation source. The laser pulse generates a high temperature micro plasma on the surface of the sample. After this excitation, light that is characteristic of the elemental composition of the sample is emitted and analyzed within a spectrometer. LIBS has become a very popular analytical method in view of some of its unique features such as applicability to any type of sample, practically no sample preparation, remote sensing capability, and speed of analysis.

A LIBS apparatus relies on the correlation between the concentration of elements and the intensity of their spectral lines to determine the composition of the target sample. Since most of the target samples are composed of many elements, which have closely spaced spectral lines in the wavelength domain, LIBS analysis requires a high wavelength precision for the spectrometer. Unfortunately, small wavelength drifts that are caused by environmental factors such as temperature and humidity variations or mechanical vibrations are unavoidable, especially for those portable LIBS apparatus which are used in field operations. These portable LIBS apparatus generally employ low resolution spectrometers without active temperature control. Yet even a tiny wavelength shift much smaller than the resolution of the spectrometer may cause large error in the predication of element concentration. Conventional solution to this issue is to utilize a standard light source (such as a mercury lamp) to perform frequent wavelength calibration. Such approach is both costly and time consuming. There thus exists a need for a LIBS apparatus which can perform wavelength calibration in a faster and more convenient way.

SUMMARY OF THE INVENTION

It is thus the goal of the present invention to provide a laser induced breakdown spectroscopy (LIBS) apparatus with automatic wavelength calibration. The LIBS apparatus comprises a database of pre-obtained LIBS spectra of standard calibration samples. When the LIBS spectrum of a target sample is acquired, a processor unit calculates a cross correlation between the LIBS spectrum of the calibration sample and the spectrum of the target sample in reference to a possible wavelength shift between the two spectra. The exact wavelength shift between the two spectra is found where the cross correlation reaches a maximum value. The wavelength shift of the target spectrum is then corrected through an interpolation procedure and the wavelength shift corrected spectrum is analyzed to obtain the composition information of the target sample.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
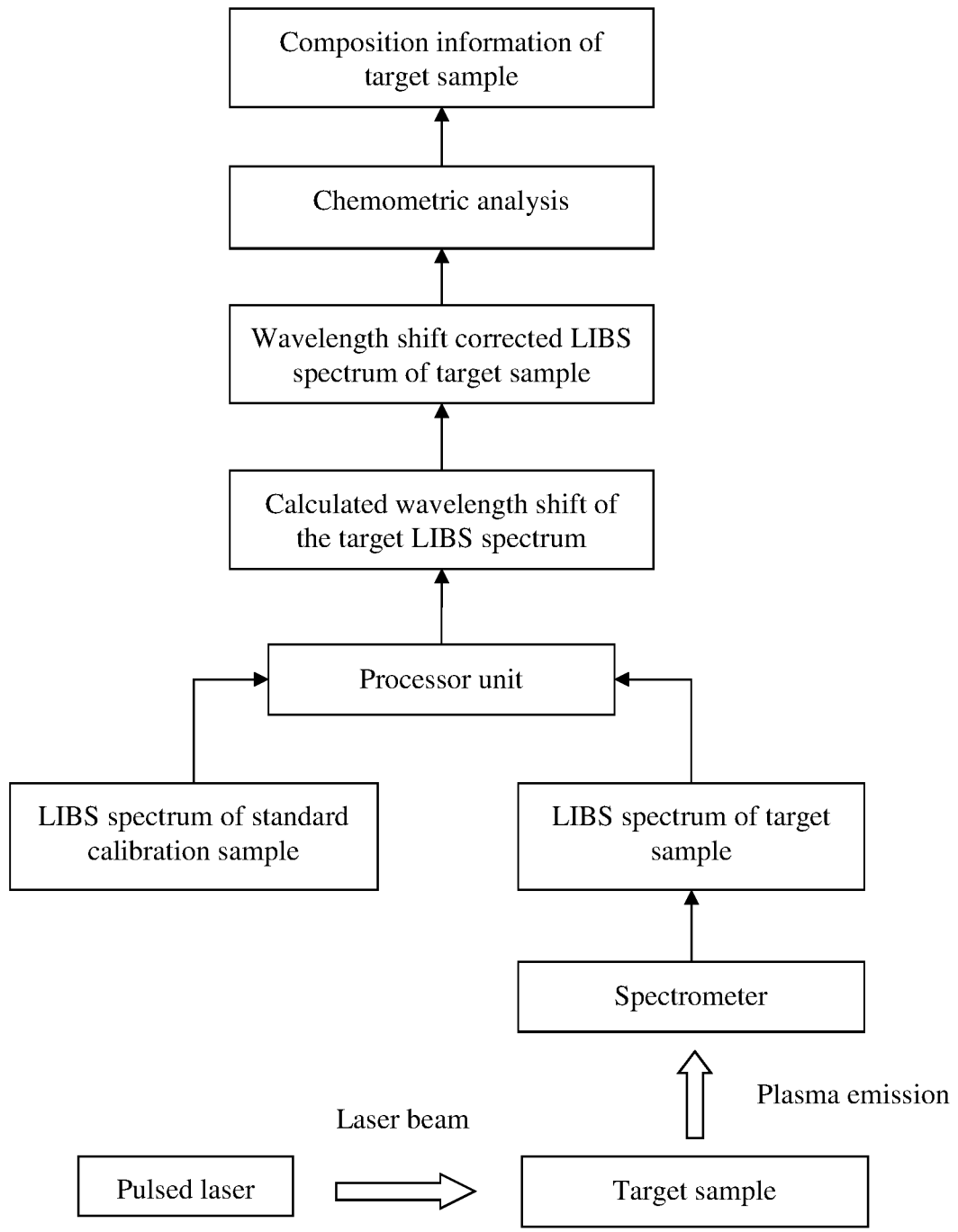
FIG. 1 is a block diagram showing the laser induced breakdown spectroscopy (LIBS) apparatus with automatic wavelength calibration.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a laser induced breakdown spectroscopy (LIBS) apparatus with automatic wavelength calibration. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

The laser induced breakdown spectroscopy (LIBS) apparatus of the present invention is preferably based on a high repetition rate pulsed laser. The laser produces a train of laser pulses at a high repetition rate in the kHz or even higher range. When the laser beam hits the sample, it generates several thousands of micro plasma emissions per second. Synchronized miniature CCD array optical spectrometer modules collect the LIBS signal from these micro plasma emissions. By adjusting the integration time of the spectrometer to cover a plurality of periods of the laser pulse train, the spectrometer integrates the LIBS signal produced by this plurality of laser pulses. Hence the intensity of the obtained LIBS spectrum can be greatly improved to increase the signal-to-noise ratio (SNR) and lower the limit of detection (LOD). In addition, the influence of pulse to pulse variation of the laser is minimized since the obtained LIBS spectrum is the spectrum of a plurality of micro plasma emissions produced by a plurality of laser pulses. The high repetition rate laser also makes it possible for fast scanning the laser beam over the sample surface such that an average spectrum of the sample is collected to overcome the sample non-uniformity issue or for performing spectral imaging of the sample by correlating the obtained LIES spectrum with the position of the scanning laser beam. A more detailed description of the high repetition rate laser based LIBS apparatus can be found in U.S. patent application Ser. No. 14/845,980, which is hereby incorporated herein by reference.

Figure 2:
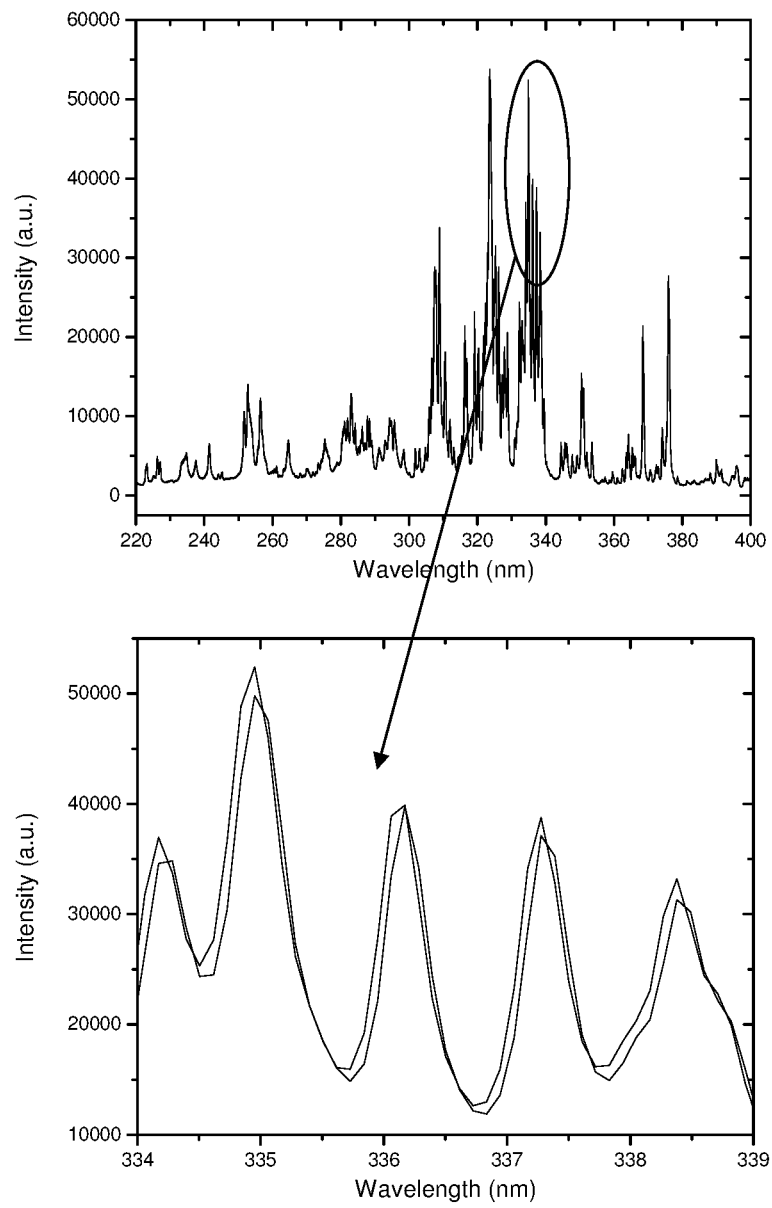
FIG. 2 shows two exemplary LIBS spectra of Ti alloys revealing the wavelength shift between the spectrum of the field measured target sample and the spectrum of the calibration sample.

FIG. 1 and FIG. 2 illustrate an exemplary embodiment of the LIBS apparatus with automatic wavelength calibration. As shown in FIG. 1, the LBS apparatus comprise a pulse laser light source, which produces a laser beam to excite plasma emission from the target sample. The plasma emission is then measured by a spectrometer device to obtain a LIBS spectrum of the target sample. To analyze the composition of an unknown target sample from its LIBS spectrum, a set of standard calibration samples with known composition are first measured with the LIBS apparatus. Based on the obtained LIBS spectral intensity and element concentration information, a calibration curve which correlates the spectral intensity with the element concentration is determined by regression analysis, which can be either univariate or multivariate analysis (such as partial least squares (PLS) analysis) or both. The composition of the target sample is then estimated based on its LIBS spectrum and the established calibration curve. The LIBS spectra of the calibration samples are generally measured in laboratory conditions, while the LIBS spectra of unknown samples are obtained in field operations. Consequently, small wavelength shifts between the two spectra, which are caused by environmental factors such as temperature and humidity variations or mechanical vibrations are usually unavoidable. As one example, FIG. 2 shows a comparison of the LIBS spectra of a field measured target sample and a calibration sample, both of which are Ti alloys. The wavelength shift between the two spectra is very small at 0.05 nm, which is even smaller than the wavelength resolution of the spectrometer at 0.12 nm. Yet such a small wavelength shift can induce large prediction error for the concentration of certain elements. This is due to the fact that both the base element and the trace elements of the Ti alloy have closely spaced spectral lines in the wavelength domain. Even a small wavelength shift can cause the spectral line of one element to be incorrectly assigned to another element. Since the calibration model relies on the intensity of the spectral lines to determine the element concentration, this will induce large prediction error for the affected element.

To correct the wavelength shift of the target sample spectrum, the LIBS apparatus of the present invention employs a processor unit to calculate a cross correlation between the LIBS spectrum of the standard calibration sample and the target sample in reference to a possible wavelength shift between the two spectra. Let $S(\lambda)$ to be the LIBS spectrum of the target sample and $R(\lambda)$ to be the LIBS spectrum of the calibration sample, the cross correlation $C(\Delta\lambda)$ between the two spectra can be expressed as:

$$C(\Delta\lambda)=\int S(\lambda+\Delta\lambda)R(\lambda)d\lambda \qquad \text{(Equation 1)}$$

where $\lambda$ is the wavelength and $\Delta\lambda$ is the possible wavelength shift between the two spectra. Here $S(\lambda+\Delta\lambda)$ can be calculated by performing interpolation (such as linear or spline interpolation) on $S(\lambda)$. The exact wavelength shift $\Delta\lambda_0$ is found where the cross correlation $C(\Delta\lambda_0)$ reaches a maximum value, which indicates that $S(\lambda+\Delta\lambda_0)$ is the wavelength shift corrected spectrum. Using the wavelength shift corrected spectrum $S(\lambda+\Delta\lambda_0)$ and the pre-established calibration curve, the composition of the target sample can be precisely predicted. It is worth noting that the target sample and the calibration sample need not to be the same type of sample. For example, they can be different Ti alloys with different trace element concentrations. The difference in their trace element concentration will not affect the calculated wavelength shift value. The advantage of the above disclosed wavelength calibration method is that the wavelength shift $\Delta\lambda_0$ can be calculated at a very high precision, which can be much higher than the wavelength resolution of the spectrometer. In addition, such wavelength calibration can be performed in real time and automatically by the processor unit for each sample spectrum collected, thus minimizing the influence of any possible change in environmental conditions. It is worth noting that the wavelength of the target LIBS spectrum needs not to be calibrated to match with an absolute wavelength standard (such as NIST atomic spectra database). Once the wavelength of the target spectrum is be calibrated to match with the wavelength of the pre-obtained calibration spectrum, the prediction based on the pre-established calibration curve will give accurate results. The wavelength calibration approach of the present invention does not require any wavelength calibration light source, which further reduces the cost of the LIBS apparatus.

Figure 3:
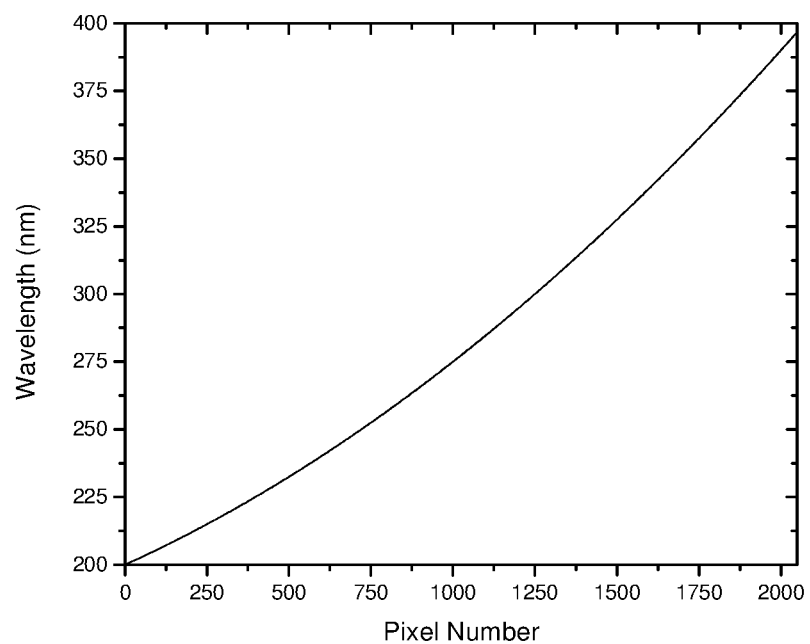
FIG. 3 shows an exemplary dispersion curve of a spectrometer device which is used for wavelength shift calculation.

In equation 1, it is assumed that the wavelength shift has the same value across the whole spectral range. i.e., the spectrometer has a linear dispersion across the pixels of its detector array. In cases where the spectrometer has a non-linear dispersion curve as shown in FIG. 3, the wavelength shift $\Delta\lambda$ in equation 1 may vary from pixel to pixel. In this case, the wavelength shift $\Delta\lambda$ for a specific pixel is proportional to the derivative of the dispersion curve at that pixel. Equation 1 shall be modified accordingly to calculate the wavelength shift corrected spectrum. Alternatively, the wavelength shift $\Delta\lambda$ can be represented by a shift in pixel number $\Delta i$ and equation 1 can be rewritten as:

$$C(\Delta i)=\Sigma S(i+\Delta i)R(i) \qquad \text{(Equation 2)}$$

where $i$ is the pixel number and $\Delta i$ is the possible pixel number shift between the two spectra. Similarly, the exact pixel number shift $\Delta i_0$ is found where the cross correlation $C(\Delta i_0)$ reaches a maximum value. The shift corrected spectrum $S(i+\Delta i_0)$ is then calculated by performing interpolation on $S(i)$ with $\Delta i_0$. Finally, the shifted corrected spectrum $S(i+\Delta i_0)$ is converted back into wavelength domain by using the dispersion curve in FIG. 3 and the converted spectrum is analyzed to extract the composition of the target sample.

In yet another approach to address the uneven wavelength shifts between the target spectrum and the reference spectrum. The whole spectrum may be separated into a plurality of spectral sections. Similar wavelength shift correction procedure as disclosed above may be applied to each spectral section where the wavelength shift is relatively consistent. The shift corrected spectral sections are then combined to form a whole shift corrected spectrum.

In both equations 1 and 2, the target spectrum S and the reference spectrum R may be normalized (such as through unit vector normalization) before calculating the cross correlation C to minimize the influence of overall spectral intensity variation.

The wavelength shift correction method of the present invention enables low resolution spectrometers to be used in LIBS apparatus. These spectrometers usually do not have the wavelength resolution to resolve individual spectral lines in the plasma emission spectrum. However, once the wavelength of the obtained LIBS spectrum is precisely calibrated using the method of the present invention, the variation in spectral line intensity will exhibit as a change in the spectral shape of the low resolution LIBS spectrum, which can be analyzed with chemometric methods such as multivariate analysis to extract the variation in element concentration. In many spectrometer configurations, a higher wavelength resolution is usually associated with a lower optical throughput. By applying the method of the present invention, an optimization of overall system performance can be achieved by designing the spectrometer with a relatively low resolution so that the spectrometer has a large optical throughput. Thus the obtained LIBS spectrum has a high signal to noise ratio (SNR) to obtain a better limit of detection (LOD).

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A laser induced breakdown spectroscopy (LIBS) apparatus for analyzing the composition of a subject, the LIBS apparatus comprising:
    a pulsed laser light source configured to produce a plasma emission from the subject;
    an optical spectrometer device configured to measure an optical spectrum of the plasma emission and obtain a LIBS spectrum of the subject;
    a database of pre-obtained LIBS spectrum by the LIBS apparatus of at least one calibration sample; and
    a processor unit configured to calculate a wavelength shift between the LIBS spectrum of the subject and the LIBS spectrum of the at least one calibration sample to obtain a wavelength shift corrected LIBS spectrum of the subject and analyze the composition of the subject from the wavelength shift corrected LIBS spectrum;
    wherein the processor unit is configured to calculate a cross correlation between the LIBS spectrum of the subject and the LIBS spectrum of the at least one calibration sample in reference to a possible wavelength shift between the two spectra and extract the wavelength shift between the two spectra where the cross correlation reaches a maximum value.

2. The laser induced breakdown spectroscopy (LIBS) apparatus of claim 1, wherein the processor unit is configured to calculate the wavelength shift corrected LIBS spectrum by performing interpolation on the LIBS spectrum of the subject with the obtained wavelength shift.

3. The laser induced breakdown spectroscopy (LIBS) apparatus of claim 1, wherein the processor unit is configured to calculate the wavelength shift at a precision higher than a wavelength resolution of the optical spectrometer.

* * * * *